United States Patent
Zhou et al.

(10) Patent No.: US 9,084,791 B2
(45) Date of Patent: Jul. 21, 2015

(54) METHOD OF INHIBITING MYOPIA AND APPLICATION OF AN ADENYLYL CYCLASE INHIBITOR AS A DRUG FOR INHIBITING MYOPIA

(75) Inventors: Xiangtian Zhou, Zhejiang (CN); Jia Qu, Zhejiang (CN); Yijin Tao, Zhejiang (CN); Miaozhen Pan, Zhejiang (CN)

(73) Assignee: SCHOOL OF OPHTHALMOLOGY AND OPTOMETRY, WENZHOU MEDICAL COLLEGE, Wenzhou, Zhejiang (CN)

( * ) Notice: Subject to any disclaimer, the term of this patent is extended or adjusted under 35 U.S.C. 154(b) by 590 days.

(21) Appl. No.: 13/513,098

(22) PCT Filed: Dec. 21, 2011

(86) PCT No.: PCT/CN2011/084332
§ 371 (c)(1),
(2), (4) Date: May 31, 2012

(87) PCT Pub. No.: WO2012/089053
PCT Pub. Date: Jul. 5, 2012

(65) Prior Publication Data
US 2012/0270887 A1    Oct. 25, 2012

(30) Foreign Application Priority Data
Dec. 27, 2010 (CN) .......................... 2010 1 0605133

(51) Int. Cl.
*A61K 31/52* (2006.01)

(52) U.S. Cl.
CPC ...................................... *A61K 31/52* (2013.01)

(58) Field of Classification Search
None
See application file for complete search history.

(56) References Cited

U.S. PATENT DOCUMENTS 5,814,638 A * 9/1998 Lee et al. .................. 514/58

FOREIGN PATENT DOCUMENTS

WO    WO 0195913 A1 * 12/2001

OTHER PUBLICATIONS

Dominguez et al., Prostaglandin E2 is an inhibitor of adenylate cyclase in rabbit proximal tubule, Am J Physiol. Feb. 1988;254(2 Pt 1):C304-9, printed from http://www.ncbi.nlm.nih.gov/pubmed/3162352, abstract only, 1 page.*
CN 201010605133.3, certified priority document, Dec. 27, 2010.*

* cited by examiner

*Primary Examiner* — Gigi Huang
(74) *Attorney, Agent, or Firm* — Osha Liang LLP

(57) ABSTRACT

Methods for inhibiting myopia are disclosed. A method for inhibiting myopia includes reducing a level of an intraocular cAMP in a subject. The level of the intraocular cAMP is reduced by injecting an adenylyl cyclase inhibitor to achieve the inhibition of myopia in the subject. In one method, the adenylyl cyclase inhibitor is SQ22536.

1 Claim, 3 Drawing Sheets

METHOD OF INHIBITING MYOPIA AND APPLICATION OF AN ADENYLYL CYCLASE INHIBITOR AS A DRUG FOR INHIBITING MYOPIA

CROSS-REFERENCE TO RELATED APPLICATIONS

This application is a national stage application based on PCT/CN2011/084332, filed on Dec. 21, 2011, entitled "A Method of Inhibiting Myopia and Application of an Adenylyl Cyclase Inhibitor as a Drug for Inhibiting Myopia," which claims priority to China Patent Application No. CN 201010605133.3, filed on Dec. 27, 2012. Both the PCT Application and Chinese Application are incorporated herein by reference in their entireties.

TECHNICAL FILED

The invention relates to a method of inhibiting myopia effectively.

BACKGROUND TECHNOLOGY

The main characteristic of human myopia is axial elongation, and the main part of axial elongation is the posterior part of eyeball. Previous studies have found that a normal human eye is significantly different from a myopic eye in collagen bundle structure, fiber diameter distribution, fiber configuration, and so on. Now, it is found that phenomena, such as thinning of the sclera, thinning of the scleral collagen fibrils, and disappearance of the gradient changes in the inner, middle and outer layers of the fiber diameters of the sclera, appear in the long-time experimental myopic eyes of mammals (e.g., tree shrew, marmoset, and guinea pig). These findings indicate that in the developmental process of myopia, the changes in the sclera structure of an myopic eye involve a positive remodeling process.

In recent years, researches on mammal myopic models (e.g., in monkey and tree shrew) showed that, in the experimental myopic eyes, growth of fibroblast is inhibited, collagen synthesis is reduced, and dry weight of sclera is reduced. Biomechanics studies also revealed that myopia resulted in a weak sclera and caused the changes in sclera stress. It is detected that the creep rate of the sclera of a myopic eye increased, the elasticity of the sclera increased, and the failure load of the tissue decreased. The above mentioned changes mainly appear in the posterior pole of the sclera. The biological and chemical changes of the sclera resulted in changes of physical and mechanical characteristics of the sclera, and eventually resulted in the development of myopia.

In conclusion, sclera is regarded as the target tissue for the occurrence and development of myopia. Hence, regulating the activation and differentiation of sclera fibroblasts may influence the occurrence and development of myopia. Kohyama T, et al. (2002) and Liu X, et al. (2004) found that regulating the intracellular cAMP (cyclic adenosine monophosphate) level may influence the activity of lung fibroblast. cAMP plays a role as a second messenger in the reaction of inhibiting the activity of fibroblasts. Differentiations of lung and cardiac fibroblasts can be inhibited by increasing the intracellular cAMP levels; conversely, activation and differentiation of lung fibroblasts can be promoted by decreasing the cAMP levels. However, at present there is no report about the effects of cAMP on sclera fibroblasts, in particular the effects of cAMP on myopia.

SUMMARY OF INVENTION

An objective of the invention is to find methods for inhibiting myopia by intervening experimental myopia through decreasing the intraocular cAMP levels.

In order to achieve above mentioned objective, embodiments of the invention adopt technical proposals as follows: inhibiting myopia by decreasing the intraocular cAMP levels.

Usually, three methods are adopted for decreasing the intraocular cAMP levels. The first method is to decrease the cAMP synthesis, e.g., decreasing the cAMP level via adenylyl cyclase (cAMP synthetase) inhibitors. At present, SQ22536 (9-(Tetrahydro-2-furanyl)-9H-purin-6-amine or 9-(tetrahydro-2-furyl)adenine) is the most commonly used adenylyl cyclase inhibitor. The second method is to increase the degradation of cAMP, e.g., decreasing the cAMP levels mainly by increasing phosphodiesterases (for hydrolyzing cAMP). The third method is to antagonize the effects of cAMP, e.g., by blocking or decreasing the effects of cAMP by antagonizing at the downstream links of cAMP effects.

The invention also provides a new drug for inhibiting myopia, namely application of the adenylyl cyclase inhibitor as a drug for inhibiting myopia.

Advantages of the invention comprise: myopia can be effectively inhibited by decreasing the intraocular cAMP levels.

In attached figures, "differences" refers to the differences of refraction or eye axis parameters between the experimental eye and the contralateral eye; comparison between the vehicle group and the drug-treated group adopts one-way analysis of variance (ANOVA): "*" refers to $P<0.05$; "" refers to $P<0.01$; "*" refers to $P<0.001$.

DETAILED DESCRIPTION

Experimental animals were 3 weeks old, UK variety, three-color and short-haired guinea pigs. Monocular form-deprivation (FD) was performed by using a facemask, and the form-deprivation eyes were treated with adenylyl cyclase inhibitor (ACI) SQ22536 at different concentrations (for example, 1 µM and 100 µM) by sub-conjunctival injection, so as to differently decrease intraocular cAMP levels. Animals were divided into 4 groups randomly: form-deprivation control group (FD+non-injection), form-deprivation+vehicle control group (FD+vehicle) (vehicle here refers to 0.9% saline), form-deprivation+drug groups (FD+1 µM SQ22536 group and FD+100 µM SQ22536 group). Drugs were sub-conjunctivally injected at 9:00 am every day for 4 weeks. The contralateral eyes were not treated. Refraction were measured with an infrared eccentric refractometer (EIR). Corneal curvature radii were measured with a keratometer. Eye axis parameters, such as vitreous chamber depths and axial lengths, were measured with an A-scan ultrasonograph (11 MHz), respectively, before experiment, 2 weeks after treatment, and 4 weeks after treatment.

After comparing measured parameters, before the experiment and after the experiment, it was found that the myopic refractive error, the vitreous chamber depths and the axial elongations of the form-deprivation eyes of the drug-treated groups were all less than those of the form-deprivation control group and the vehicle control group, and the comparison with the vehicle control group had statistic significance. Therefore, the formation of form-deprivation myopia of guinea pigs could be inhibited by decreasing intraocular cAMP levels through sub-conjunctival injection of an adenylyl cyclase inhibitor (ACI) SQ22536.

Figure 1:
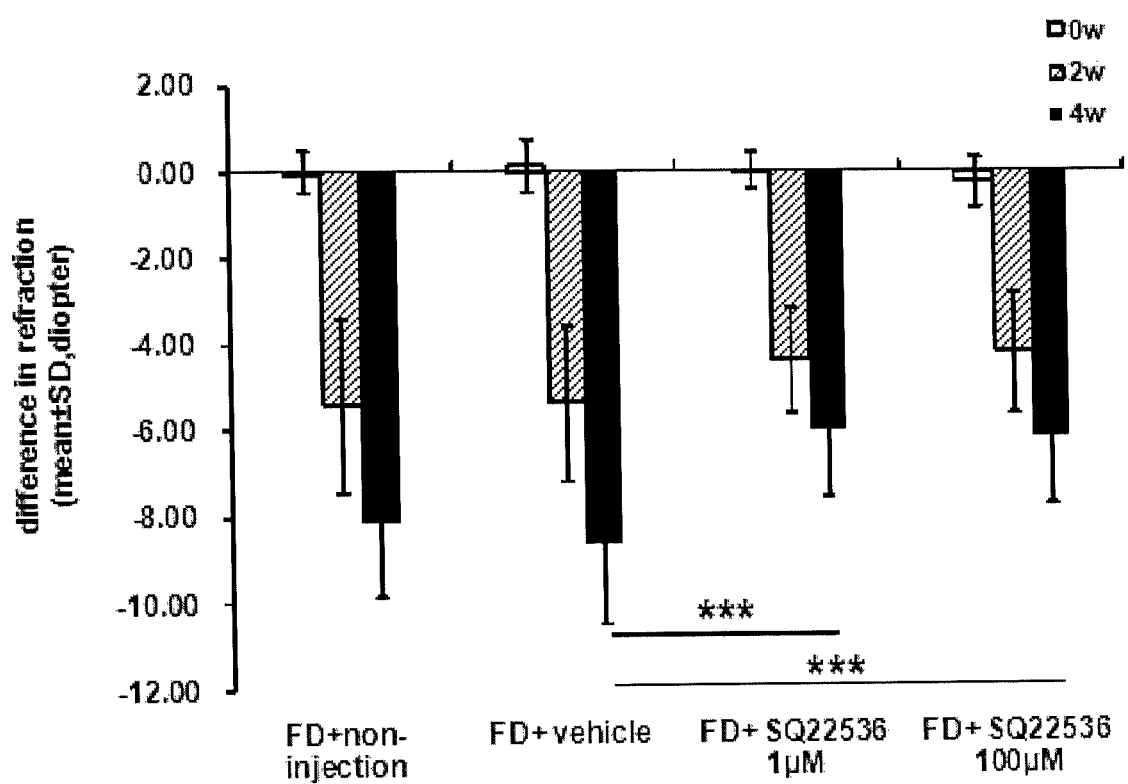
FIG. 1 shows a diagram of refraction differences between an experimental eye and a contralateral eye.

As shown in FIG. 1, after 4 weeks of experiment, the myopic refractive error between the form-deprivation control group and the form-deprivation and vehicle injection control group had no difference. Thus, it showed that injection had no influence on form-deprivation. The myopic refractive errors of the two drug-treated groups were all less than that of the vehicle control group. There were a time-dependent effect and a concentration dependent effect. It showed that adenylyl cyclase inhibitor SQ22536 could inhibit the formation of form-deprivation myopia.

Figure 2:
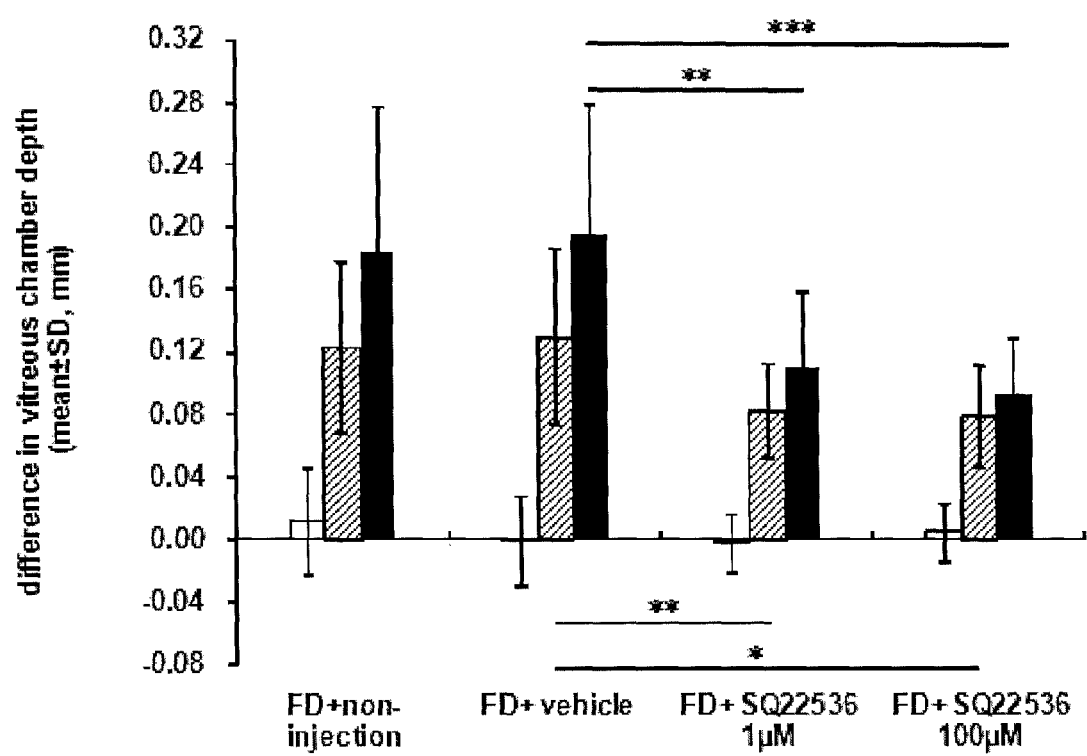
FIG. 2 shows a diagram of vitreous chamber depth differences between an experimental eye and a contralateral eye.

As shown in FIG. 2, after 4 weeks of experiment, the vitreous chamber elongations between the form-deprivation control group and the form-deprivation and vehicle injection control group had no difference, indicating that injection had no influence on form-deprivation. The vitreous chamber elongations of the two drug-treated groups were significantly less than that of the vehicle control group. There were a time-dependent effect and a concentration dependent effect. It showed that adenylyl cyclase inhibitor SQ22536 could inhibit the elongation of vitreous chamber in form-deprivation.

Figure 3:
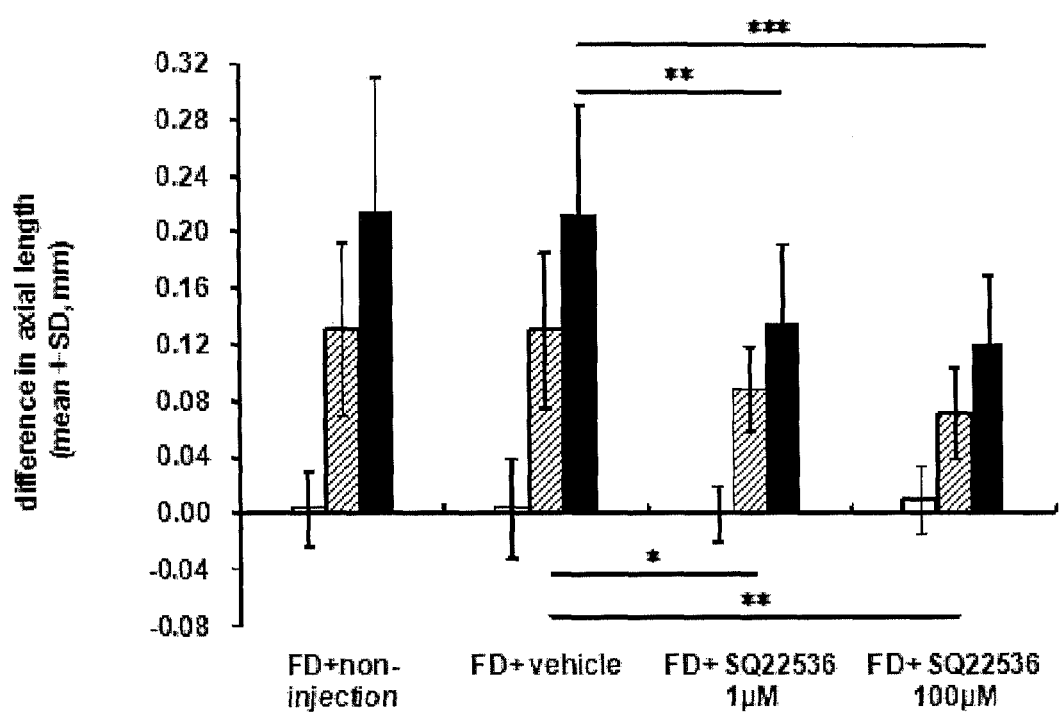
FIG. 3 shows a diagram of axial length differences between an experimental eye and a contralateral eye.

As shown in FIG. 3, after 4 weeks of experiment, the axial elongations between the form-deprivation control group and the form-deprivation and vehicle injection control group had no difference, indicating that injection had no influence on form-deprivation. The axial elongations of the wo drug-treated groups were significantly less than that of the vehicle control group. There were a time-dependent effect and a concentration dependent effect. It showed that adenylyl cyclase inhibitor SQ22536 can inhibit the elongation of eye axis in form-deprivation.

The above experimental results demonstrated that myopia could be significantly inhibited by reducing the cAMP levels with an adenylyl cyclase inhibitor.

The invention claimed is:

1. A method for inhibiting myopia, comprising reducing a level of an intraocular cAMP in a subject by subconjunctival injection of an adenylyl cyclase inhibitor, wherein the adenylyl cyclase inhibitor is 9-(tetrahydro-2-furyl)adenine (SQ22536).

* * * * *